(12) United States Patent
Le Neel

(10) Patent No.: US 8,219,771 B2
(45) Date of Patent: Jul. 10, 2012

(54) PORTABLE DEVICE FOR STORING PRIVATE INFORMATION SUCH AS MEDICAL, FINANCIAL OR EMERGENCY INFORMATION

(75) Inventor: Olivier Le Neel, Irving, TX (US)

(73) Assignee: STMicroelectronics, Inc., Coppell, TX (US)

( * ) Notice: Subject to any disclaimer, the term of this patent is extended or adjusted under 35 U.S.C. 154(b) by 337 days.

(21) Appl. No.: 11/583,746

(22) Filed: Oct. 19, 2006

(65) Prior Publication Data

US 2008/0094926 A1    Apr. 24, 2008

(51) Int. Cl.
G06F 12/00    (2006.01)
G06F 13/00    (2006.01)
G06F 13/28    (2006.01)

(52) U.S. Cl. ........................................................ 711/163
(58) Field of Classification Search .................. None
See application file for complete search history.

(56) References Cited

U.S. PATENT DOCUMENTS

2003/0216954 A1* 11/2003 Buzzelli ........................... 705/10
2004/0255081 A1* 12/2004 Arnouse ........................ 711/115
2006/0016877 A1* 1/2006 Bonalle et al. ................ 235/380

OTHER PUBLICATIONS

Langendoerfer et al., Towards User Defined Privacy in Location-Aware Platforms, 2002, Proceedings of the 3rd International Conference on Internet Computing, 7 pages.*
Vachharajani et al., RIFLE: An Architectural Framework for User-Centric Information-Flow Security, 2004, IEEE, 12 pages.*

* cited by examiner

*Primary Examiner* — Kevin Ellis
*Assistant Examiner* — Gary W Cygiel
(74) *Attorney, Agent, or Firm* — Gardere Wynne Sewell LLP

(57) ABSTRACT

A portable housing capable of being carried by a certain person includes a circuit. The circuit includes a memory for storing private data concerning that certain person, a circuit operable to effectuate storage of the private data in the memory in a secure manner, and a processing unit operable to control access to the memory for purposes of reading private data concerning the certain person from the memory and storing private data concerning the certain person to the memory. The conditions under which access to the memory for read and write operations with respect to the private data is permitted are governed by parameters that are specified by the certain person to whom the stored private data concerns. A biometric sensor may also be included to capture identification information useful in implementing the operations for controlling access to the memory.

21 Claims, 1 Drawing Sheet

PORTABLE DEVICE FOR STORING PRIVATE INFORMATION SUCH AS MEDICAL, FINANCIAL OR EMERGENCY INFORMATION

BACKGROUND OF THE INVENTION

1. Technical Field of the Invention

The present invention relates to portable data storage devices and, more particularly, to a portable mass storage device for storing private information. Examples of such private information include personal medical information, financial information and emergency information.

2. Description of Related Art

Persons are associated with a tremendous amount of private information. By this it is meant information that is typically unique to the person and is very often sensitive personal information that the person generally would prefer to keep to themselves and make available to others only in certain situations. An example of this would be personal medical information such as medical histories both of themselves and family members, medical conditions, treatment histories, drug and allergy information, and the like. Another example would be personal financial information such as account information, investment information, balance and transaction information, strategy information, access codes, numbers and authorizations. Yet another example would be emergency information such as an identification of an emergency contact or an identification of relatives with address and phone number data. A still further example would be personal information such as birth records, passport data, drivers license data, identification data, social security data, immigration data, and the like.

In any case, the voluminous amount of private information associated with each person could occupy many pages of paper and in such a format would be most difficult for the person to carry with them. Historically, this issue has been addressed in part by having the private information be stored and maintained by the person and/or a third party. For example, a person's medical information is most often stored and maintained by that person's physician or local hospital. Likewise, a person's financial information is most often stored and maintained by that person's bank, financial institution, investment counselor, or lawyer. It is also quite common for persons to additionally keep such financial information themselves in personal files kept at home. This is contrasted with personal medical information which is rarely if ever kept to any significant degree by the patient. With respect to emergency information and personal information, this information is, like financial information, most often maintained by the person in their own files, although many persons additionally store such information in the hands of family members and lawyers.

Nonetheless, it will be noted that most of the information is not physically carried by the person as they go about their daily business. The amount of information is simply too large to conveniently carry. Additionally, even if the information could be carried by the person, it is generally not secured and thus if misplaced or stolen could give a criminal access to certain pieces of information which would facilitate criminal and/fraudulent activity, or grant a third party access to private information which the person would prefer not to be known by others (such as net worth financial data, or medical condition data).

Although an infrequent occurrence, there are times when it is critical that the private information be available to the person or authorized third parties. Take, for example, the situation where the person is traveling for business or pleasure and suffers a medical emergency. In such a situation it would be helpful to a caregiver if that person's medical information were immediately available for review. As discussed above, most persons do not carry their medical histories with them and thus the caregiver would have to rely on the person's memory to recall their medical history, or wait until the person's doctor could be contacted. This problem is further complicated if the person's medical condition renders them incapacitated (for example, unconscious) and thus unable to actively participate in the rendering of medical aid.

A need exists in the art for a way to allow persons to store large amounts of private information, such as personal medical information, financial information and/or emergency information, in a portable device which would not only provide for the secure storage of the private information but also allow the person to specify in advance, and thus exercise control over, the conditions under which third parties would be able to access the securely stored private information from the portable device.

SUMMARY OF THE INVENTION

In an embodiment, a device comprises a portable housing capable of being carried by a certain person, and a circuit within the portable housing. The circuit comprises a memory for storing private data concerning that certain person, a circuit operable to effectuate storage of the private data in the memory in a secure manner, and a processing unit operable to control access to the memory for purposes of reading private data concerning the certain person from the memory and storing private data concerning the certain person to the memory. The conditions under which access to the memory for read and write operations with respect to the private data is permitted are governed by parameters that are specified by the certain person to whom the stored private data concerns.

In another embodiment, a system comprises a portable device for storing private data concerning a certain person, a personal computing device; and a communications link interconnecting the personal computing device and the portable device, the communications link carrying private data concerning that certain person for transmission to the portable device or for transmission from the portable device. The portable device comprises a circuit within a portable housing comprising a memory for storing the private data concerning that certain person, a circuit operable to effectuate storage of the private data in the memory in a secure manner, and a processing unit operable to control access to the memory for purposes of reading private data concerning the certain person from the memory and storing private data concerning the certain person to the memory. The conditions under which access to the memory for read and write operations with respect to the private data is permitted are governed by parameters specified and entered by the certain person to whom the stored private data concerns through personal computing device and communicated over the communications link.

BRIEF DESCRIPTION OF THE DRAWINGS

A more complete understanding of the method and apparatus of the present invention may be acquired by reference to the following Detailed Description when taken in conjunction with the accompanying Drawings wherein.

DETAILED DESCRIPTION OF THE DRAWINGS

Figure 1:
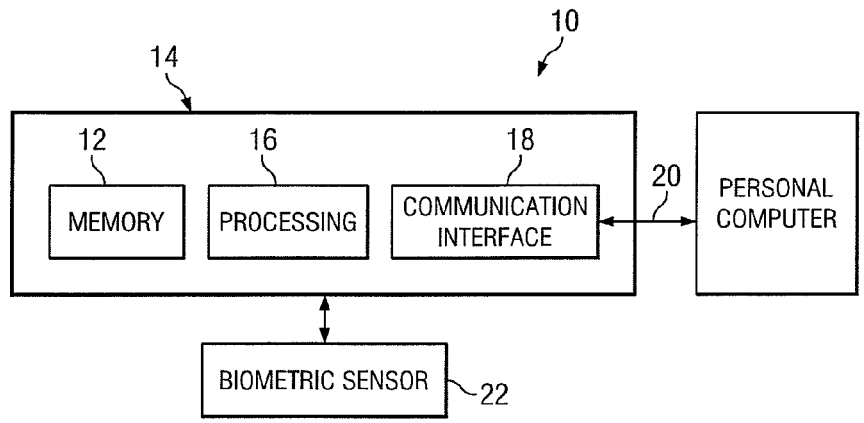
FIG. 1 is a block diagram of a system implementation of the present invention.

An aspect of the present invention concerns enabling individual persons to own a private database in a portable format, wherein the database is capable of storing large amounts of private information in a secure way. While a primary application for the database is the storage of personal medical information, it will be understood that the database can store any information of a personal or confidential manner as desired by the owner. Generally speaking, this information would be considered private to the person. It will be understood, however, that private in this context does not necessarily mean that the information is secret information, or is information that would necessarily need to be hidden from others. Rather, private information refers to information that is owned by the person and whose dissemination is controlled by the person in accordance with some predefined agreement, authorization or condition.

Historically speaking, security-based applications with respect to data have been based on two concepts. First, although the data may relate to a person, that data is owned by an organization other than the person (for example, a doctor, hospital, bank, etc.), and the organization defines the rules which must be followed in order for access to that data to be granted (for example, a signed release, a PIN number, etc.). Second, even though the data is the person's data, that person is given access to the data only through the use of an identification mechanism (like the PIN, or presentation of a driver's license) as specified by the organization.

The present invention implements a reversal in the ownership scheme with respect to such data from the organization to the individual in an organized and highly secured environment. To implement this, the present invention recognizes the person as the owner of the data, and allows the owner/person to decide how and when (i.e., under what circumstances) others such as third parties, including the organizations noted above, are to be granted access to the data.

Thus, the owner of the data is allowed to grant third party access to the data in accordance with their own personal decision. In other words, the person to whom the data concerns specifies the conditions under which a third party may access the data, including specifying the degree to which different third parties may retrieve the stored data. This third party access to the data is always given by the predetermined and specified choice (i.e., direction) of the person owning the data, and it is the responsibility of that person to specify all parameters governing third party access to the data. It will be recognized that access to some stored data may be required in certain emergency situations (such as emergency contact data) and that the person should not necessarily be able to control and restrict access to the data by legitimate third parties (for example, a governmental entity such as the police). In all other cases where the personal security of the person/owner would be at risk, the person who owns the data pre-defines the level of third party access rights.

This may be analogized in a way to a person's home. The home is private property and the homeowner can predefine the nature and extent to which third parties such as relatives, friends or a housekeeper are given access to the private property through access to keys and security codes, but the homeowner nonetheless grants a governmental entity such as the fire department access to the home in the event of an emergency. Likewise, with respect to the stored private data, certain keys can be predefined by the person/owner which govern when and to what extent third parties may access the stored data, but nonetheless the person/owner would grant governmental emergency services personnel access to certain data in the event of an emergency situation.

As a further example, consideration may be given to personal medical data. It is recognized that a person's body is their own property and medical information relating to that person's body is likewise the property of the person. A person would authorize others such as doctors, nurses, hospitals, clinics access to their body in order to perform medical analyses. The medical information and data which result from such analyses belong to the person being examined. Thus, diagnostic and treatment data for a person belong to that person. An organization, such as a doctor or an insurance company, may be given access to the stored record of medical information or data for certain predefined purposes, wherein access to the data is granted by area and with respect to predetermined topics as specified by the person/owner of the data. In this way, a doctor can be given one level of data access (perhaps complete access), while an insurance company or employer is give another more restricted level of access. In this way, the person/owner can define the level of access and privacy desired. Additionally, in an emergency situation, a government agency might be granted authorization to a certain level of data, while in non-emergency situations the level of access could be more restricted.

Consider now the portable data storage device which stores the database of personal medical information (data). As an example, this portable data storage device could comprise a "smart card" type of technology known in the art. The person/owner can decide the conditions under which a doctor is granted access to the database. For example, in one scenario, the person may authorize the doctor read-only rights with respect to already stored information, but otherwise the doctor may only write to the database so as to store new data but cannot modify prior data. This may be appropriate, for example, when the person is seeing a doctor other than his/her normal attending physician. In another scenario, the doctor may be authorized by the person to access the database for any read/write operation. In either case, it is the person who owns the data about themselves who can specify the level of access. This may be specified in advance through stored access parameters, or alternatively specified in real time using some sort of keyed authorization such as the entry of a PIN code or through a biometric scan.

The foregoing addresses the situation where a third party is granted access to the database on the portable data storage device. It will also be noted that situations may often arise wherein the person desires access to the database. In this case, access to the database for read/write purposes may be governed by some sort of keyed authorization such as the entry of a PIN code or through a biometric scan.

In any case, it is the owner of the information/data who is making the decision (either in real time or predetermined) as to whom is given access to their private information and under what circumstances and conditions that access is to be granted. Additionally, it will be noted that ownership of the data never changes from the person. The person remains in control of the database and its contained information/data.

Reference is now made to FIG. 1 wherein there is shown a block diagram of a system implementation of the present invention. A portable data storage device 10 is provided which includes a mass storage data memory 12, for example of a size at or greater than 1 Gbit, although it will be understood that certain implementations may not require a memory that large. The portable data storage device 10 may take on any one of a number of known physical formats. A preferred implementation would utilize "smart card" technology thus allowing the device 10 to be carried by the person in a manner similar to the way the person would carry a credit card or other identification card. Another implementation would utilize "key fob" technology thus allowing the device 10 to be carried by the person along with their house and car keys.

The memory 12 is implemented within an integrated circuit chip 14 that is contained within the housing of the device 10 in a manner well known in the art. The integrated circuit preferably includes the memory 12 implemented, for example, as a NAND-based FLASH memory. The integrated circuit 14 further includes processing circuitry 16 and communications/interface circuitry 18. The integrated circuit 14 may in an implementation comprise an ASIC circuit or a microcontroller circuit which includes embedded memory 12. The processing circuitry 16 is operable to execute an application program which governs operation of the device 10. The application program may be stored in memory 12, or alternatively stored in a separate programming memory (such as EEPROM) associated with the processing circuitry 16. The communications/interface circuitry 18 functions to support external data communication with respect to the device 10. Modes of communication which may be supported by the communications/interface circuitry 18 include one or more wireless and/or wireline communication technologies known in the art such as RF communications and USB communications. As an example, the communications/interface circuitry 18 may comprise a "smart card" reader circuit supporting "smart card" data communications with the device 10. Utilizing a data communications link 20 supported by the communications/interface circuitry 18, the processing circuitry 16 can transmit data from the device 10 (as extracted from the memory 12) as well as receive data to the device (for storage in the memory). The other end of the data communications link 20 may be coupled in a known manner to a personal computing device (such as a laptop or other data processor). An application for supporting data communication over the data communications link 20 would be executed by the personal computing device in order to support the transmission of data to the device 10 (for storage in the memory 12) as well as to receive data from the device (as retrieved from storage in the memory).

In an implementation, the device 10 may further include a biometric sensor 22 communicatively coupled to the integrated circuit 14, for example to the processing circuitry 16. The biometric sensor 22 may preferably comprise a fingerprint sensor (for example, of the capacitive-type known in the art) which functions to obtain biometric data. This captured biometric data is processed by the processing circuitry 16 for the purpose of identifying the person/owner of the device 10 (i.e., the person/owner of the information/data which is stored in the memory 12). To this end, application software is stored on the device 10 and executed by the processing circuitry 16 to perform identification operations with respect to the person/owner of the device 10.

Figure 2:
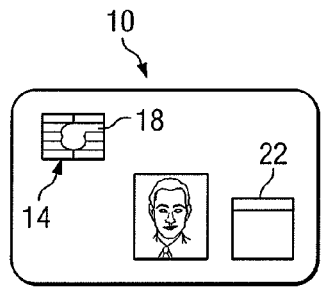
FIG. 2 illustrates a format for one embodiment of the smart card based device.

FIG. 2 illustrates a format for one embodiment of the smart card based device 10. In this embodiment, it will be noted that the integrated circuit smart card chip 14 is embedded within the housing of the device 10. The chip 14 would include the processing, memory and communications circuitry needed for supporting device operation. The housing of the device would further contain the biometric sensor 22 in the form, for example, of a fingerprint reader. The sensor 22 would be coupled to the integrated circuit smart card chip 14. It will be recognized that that it is also possible to integrate the sensor 22 within the chip 14. Communication to and from the device 10 in this implementation would be made wirelessly for example using known smart card reader technology. Using the wireless communications link of the smart card reader, the person/owner of the device 10, as well as a third party, can easily interface the device 10 with a personal computer to facilitate information/data exchange.

Figure 3:
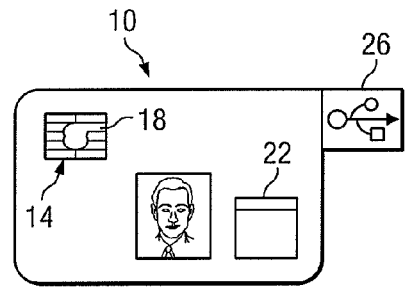
FIG. 3 illustrates a format for another embodiment of the smart card based device.

FIG. 3 illustrates a format for another embodiment of the smart card based device 10. In this embodiment, it will be noted that the integrated circuit smart card chip 14 is embedded within the housing of the device 10. The chip 14 would include the processing, memory and communications circuitry needed for supporting device operation. The housing of the device would further contain the biometric sensor 22 in the form, for example, of a fingerprint reader. The sensor 22 would be coupled to the integrated circuit smart card chip 14. It will be recognized that that it is also possible to integrate the sensor 22 within the chip 14. Communication to and from the device 10 in this implementation would be made in a wireline fashion using a USB port 26 positioned along an edge of the device housing. Using the USB port 26, the person/owner of the device 10, as well as a third party, can easily interface the device 10 with a personal computer to facilitate information/data exchange.

The memory 12 supports personal information/data storage on the device 10 in any one of a number of formats. In a preferred implementation, the personal information/data is stored in the memory 12 of the device 10 in a database format (for example, a relational database format). Other data storage formats known to those skilled in the art could be used. In addition, a combination of data storage formats may be used wherein the selected format is tailored to the kind of data being stored as well as to the read/write actions anticipated with respect to that data.

The person/owner of the device 10 would act to configure their device 10 in the manner they choose with respect to the issue of how and when (i.e., under what circumstances) they as well as others such as third parties including the organizations noted above are to be granted access to the data. This can be accomplished by setting certain parameters and storing the parameter data in the device 10. The application executed by the processing circuitry 16 would evaluate these set parameters, in the context of the requested access, in order to determine whether access to the memory 12 should be granted, and if so to what degree access is permitted. The degree in this context refers to what files can be accessed as well as whether read, write, or both access is being granted.

The foregoing may be better understood by reference to an example concerning entering personal medical data into the device 10 for storage in the memory. The person/owner may set certain access parameters for a doctor or pharmacy. The access parameters may permit a doctor or pharmacist (or their assistant) to be able to access the memory 12 for the purpose of writing data to only certain fields. For example, the parameters processed by the processing circuitry 16 may give a doctor broader write access permission as to any medical record area, while the pharmacist is permitted by the parameters write access only with respect to a record area where pharmaceutical information is stored (prescriptions written, drugs taken, allergies, etc.). It should be noted that it is the person/owner of the device and information which sets these write parameters, not the doctor or pharmacist. With respect to the person/owner, write control parameters may be defined which grant the person complete write access to their stored information. Alternatively, the parameters may restrict the person/owner write access to certain fields or areas so as to eliminate the risk of the person/owner accidentally changing critical medical data as entered by the doctor or pharmacist. Again, it is the person/owner of the device and information which sets these write parameters.

The parameters may further define what type of authentication is required in order for access to be granted. For example, with respect to the person/owner those parameters may specify, for devices which include a biometric sensor 22 that the request for access include a biometric authentication of the person. Alternatively, the parameters may specify that the request for access include an entered authentication code or PIN associated with the entity making the access request. A combination of biometric and PIN may be required.

Moving next to an example concerning retrieving personal medical data from the device 10 and its memory, the person/owner may set certain access parameters for a doctor or pharmacy. The access parameters may permit a doctor or pharmacist (or their assistant) to be able to access the memory 12 for the purpose of reading data from only certain fields. For example, the parameters processed by the processing circuitry 16 may give a doctor broader read access permission as to any medical record area, while the pharmacist is permitted by the parameters read access only with respect to a record area where pharmaceutical information is stored (prescriptions written, drugs taken, allergies, etc.) as well as the medical records relating to medical conditions and physician orders and prescriptions. It should be noted that it is the person/owner of the device and information which sets these write parameters, not the doctor or pharmacist. With respect to the person/owner, read control parameters may be defined which generally grant the person complete read access to their stored information. With respect to other third parties, such as emergency personnel, the parameters may restrict the third party read access to certain fields or areas associated with the provision of emergency medical care so as to eliminate the risk of the third party gaining access to private information that the person/owner wishes to keep confidential. Again, it is the person/owner of the device and information which sets these read parameters.

As with the write information, the parameters may further define what type of authentication is required in order for read access to be granted. For example, with respect to the person/owner those parameters may specify, for devices which include a biometric sensor 22 that the request for access include a biometric authentication of the person. It will be noted that even in the event of an emergency where the person/owner was unconscious the ability to biometrically authenticate through a fingerprint may still be performed thus granting the doctor/hospital complete access to the stored medical information. Alternatively, the parameters may specify that the request for access include an entered authentication code or PIN associated with the entity making the access request. A combination of biometric and PIN may be required. In still other situations, the parameters may specify that the request for access need not include any special authentication (but in such situations the parameters would further restrict the third party read access to certain fields or areas, such as in the case of the provision of emergency medical care).

It was mentioned above that the device includes an application executed by the processing circuitry 16. It will be noted that an "application" could mean more than one program or computer application for execution on and by the device 10. The application(s) executed on the device should function:
  to include readers inside the device supporting reading by desktop and laptop personal computers;
  to support reading files compliant with Internet-like applications;
  to organize files in a way which follows pertinent file reading standards associated with standard browsers;
  to support the definition and formatting of files in a manner accessible only using a proprietary application executing on the personal computer;
  to support conversion of files between formats;
  with a main application capable of reading all file types and operable to convert files in a format allowing for database creation and support operation of a search engine;
  to support data organization and search engine functions;
  to support organization of the data in a way which supports information searches;
  to support file management, key definition and tagging useful in organizing the database; and
  to support specific files for the application with tags and/or specific extensions.

It was further mentioned above that the personal computer includes an executing application supporting access to the device 10. It will be noted that an "application" could mean more than one program or computer application for execution on and by the personal computer. The application(s) executed on the personal computer should function:
  to support organization of the data in a way which supports information searches;
  to support file management, key definition and tagging useful in organizing the database; and
  to support specific files for the application with tags and/or specific extensions.

Figure 4:
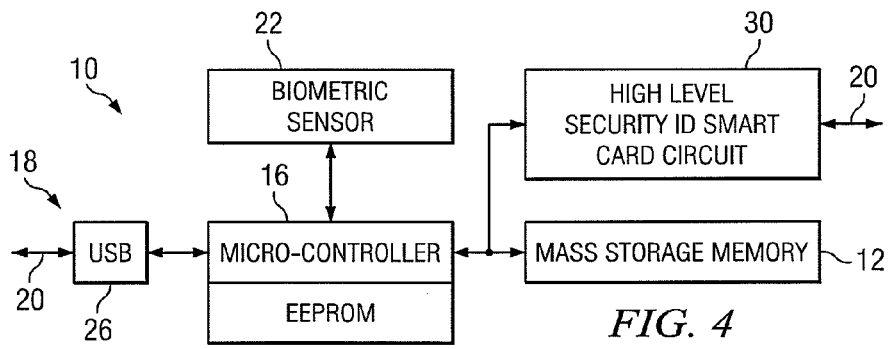
FIG. 4 is a block diagram of an embodiment of the present invention.

Reference is now made to FIG. 4 wherein there is shown a block diagram of an embodiment of the present invention. The portable data storage device 10 is housed using a smart card-type housing within which is provided a >1 Gbit mass storage data memory 12. The memory may comprise, for example, a NAND FLASH memory implemented as an integrated circuit or a hard-drive memory. The memory 12 operates to store information/data preferably in a file and/or database organized format. The portable data storage device 10 further includes a microcontroller (processing circuitry) 16 with EEPROM (such as the ST16 or ST19 devices available from STMicroelectronics) which is coupled to the mass storage data memory 12. Browser code or a Java applet executing on the personal computer supports a functionality for externally reading the microcontroller. Thus, it will be recognized that the microcontroller supports PC reader emulation. The portable data storage device 10 further includes a high level security ID smart card integrated circuit 30 interfaced with the mass storage data memory 12 and the microcontroller (processing circuitry) 16. The smart card circuit 30 functions in a manner known in the art to secure access to data stored in the mass storage data memory 12 via PIN number, password or other authentication and scramble data organization on memory access such that the memory 12 cannot be read without the presence and approval of the smart card integrated circuit 30. The smart card circuit 30 may further include communications/interface circuitry 18 supporting a data communications link 20 over which data can be transmitted from the device 10 (as extracted from the memory 12) as well transmitted to the device (for storage in the memory). The portable data storage device 10 may further include a biometric sensor 22 communicatively coupled to the processing circuitry 16. The sensor 22 is preferably a touch-chip fingerprint sensor which can be configured and is operable to identify one or more persons based on their unique fingerprint patterns. The processing circuitry 16 may further support communications/interface circuitry 18 supporting a data communications link 20, using USB-based wireline communications technology, over which data can be transmitted from the device 10 (as extracted from the memory 12) as well transmitted to the device (for storage in the memory).

The memory 12, microcontroller (processing circuitry) 16, smart card circuit 30 and sensor 22 may be implemented as separate integrated circuits and/or components within the smart card housing. Alternatively, some integration of multiple ones of the circuits together may also be provided.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. A portable device, comprising:
    a housing for the portable device capable of being carried by a certain person and in the form of a smart card; and
    a circuit contained within the smart card housing, the circuit comprising:
        a communications interface circuit;
        a memory operable to store private data concerning that certain person and for storing third party access parameters defining a plurality of restricted levels of third party read/write access to the memory for read and write operations with respect to the stored private data based on who the third party is, wherein relationships between the restricted level and who the third party is are specified and stored into the memory by that certain person to which the stored private data concerns; and
        a processing unit coupled to the communications interface circuit and the memory, the processing unit operable, in response to communications interface circuit receipt of a third party request for access to the memory, to:
            evaluate the third party access parameters stored in the memory in the context of the third party request for access to the memory;
            select one of the plurality of levels of third party read/write access to the memory; and
            control requesting third party reading of private data concerning the certain person from the portable device's memory through the communications interface circuit and controlling requesting third party writing of private data concerning the certain person to the portable device's memory through the communications interface circuit based on the selected level of third party read/write access.

2. The device of claim 1, further comprising a storage circuit operable to effectuate storage of the private data in the memory in a secure manner.

3. The device of claim 2, wherein the storage circuit operable to effectuate storage of the private data in the memory in a secure manner comprises a circuit that scrambles the private data for storage on the memory.

4. The device of claim 2, wherein the storage circuit operable to effectuate storage of the private data in the memory in a secure manner comprises a security identification smart card circuit.

5. The device of claim 1, wherein the programmed third party access parameters comprise authentication parameters which are evaluated by the processing unit in the context of the third party request for access to the memory to select one of the plurality of levels of third party read/write access to the memory.

6. The device of claim 1, further comprising a biometric scanner coupled to the processing unit and operable to receive biometric identification information which is evaluated by the processing unit to identify that certain person to which the stored private data concerns.

7. The device of claim 1, further comprising means coupled to the processing unit for receiving identification information which is evaluated by the processing unit to identify that certain person to which the stored private data concerns.

8. The device of claim 1, wherein the smart card housing has a size and shape of either a credit card or a key fob.

9. The device of claim 1, wherein the private data concerning that certain person comprises at least one of personal medical information, personal financial information and personal emergency information of that certain person.

10. The device of claim 1, wherein the plurality of restricted levels of third party read/write access include:
    a first level associated with a first type of third party, wherein the first level permits access by the first type of third party to the memory with respect to first certain ones of the files of the private data; and
    a second level associated with a second type of third party, wherein the second level permits access to the memory by the second type of third party with respect to second certain ones of the files of the private data different from the first certain ones of the files.

11. The device of claim 1, wherein the plurality of restricted levels of third party read/write access include:
    a first level associated with a first type of third party, wherein the first level permits access to the memory by the first type of third party with respect to first certain ones of the files of the private data; and
    a second level associated with a second type of third party, wherein the second level permits access to the memory by the second type of third party with respect to the first certain ones of the files of the private data and second certain ones of the files of the private data different from the first certain ones of the files.

12. The device of claim 1, wherein the plurality of restricted levels of third party read/write access include:
    a first level associated with a first type of third party, wherein the first level permits read only access to the memory by the first type of third party with respect to first certain ones of the files of the private data; and
    a second level associated with a second type of third party, wherein the second level permits both read and write access to the memory by the second type of third party with respect to the first certain ones of the files.

13. The device of claim 12, wherein the plurality of restricted levels of third party read/write access further include:
    a third level associated with the second type of third party, wherein the third level permits read only access to the memory by the second type of third party with respect to third certain ones of the files of the private data different from the first and second certain ones of the files of the private data.

14. A method, comprising:
    storing, in a memory contained within a housing for a portable smart card device capable of being carried by a certain person, private data concerning that certain person;
    storing, in the memory, third party access parameters defining a plurality of restricted levels of third party read/write access to the memory for read and write operations with respect to the stored private data based on who the third party is;

wherein relationships between the restricted level and who the third party is are specified and stored in the memory by that certain person to which the stored private data concerns;

receiving at the portable smart card device a third party request for access to the memory;

evaluating by the portable smart card device third party access parameters stored in the memory in the context of the third party request for access to the memory;

selecting by the portable smart card device one of the plurality of levels of third party read/write access to the memory;

controlling by the portable smart card device a reading of private data concerning the certain person from the memory by the requesting third party based on the selected level of third party read/write access; and controlling by the portable smart card device a writing of private data concerning the certain person to the memory by the requesting third party based on the selected level of third party read/write access.

15. The method of claim 14, further comprising storing the private data in the memory in a secure manner.

16. The method of claim 14, wherein the programmed third party access parameters comprise authentication parameters, the method further comprising evaluating the authentication parameters in the context of the third party request for access to the memory and selecting one of the plurality of levels of third party read/write access to the memory based on that evaluation.

17. The method of claim 14, further comprising receiving biometric identification information; evaluating the biometric identification information; and identifying that certain person to which the stored private data concerns in response to the evaluation.

18. A system, comprising:
a portable smart card device;
a personal computing device;
a communications link interconnecting the personal computing device and the portable smart card device;
wherein the portable smart card device comprises:
a housing for the portable smart card device capable of being carried by a certain person; and
a circuit contained within the portable housing of the portable smart card device, the circuit comprising:
a communications interface circuit;
a memory operable to store private data concerning that certain person and for storing third party access parameters defining a plurality of restricted levels of third party read/write access to the memory for read and write operations with respect to the stored private data based on who the third party is, wherein relationships between the restricted level and who the third party is are specified and stored into the memory by that certain person to which the stored private data concerns; and
a processing unit coupled to the communications interface circuit and the memory, the processing unit operable, in response to communications interface circuit receipt of a third party request for access to the memory, to:
evaluate the third party access parameters stored in the memory in the context of the third party request for access to the memory;
select one of the plurality of levels of third party read/write access to the memory; and
control requesting third party reading of private data concerning the certain person from the memory and controlling requesting third party writing of private data concerning the certain person to the memory based on the selected level of third party read/write access;
wherein the communications link carries the private data concerning that certain person for transmission to the portable device or for transmission from the portable smart card device.

19. The system of claim 18, wherein the programmed third party access parameters comprise authentication parameters, the processing unit evaluating the authentication parameters in the context of the third party request for access to the memory to select one of the plurality of levels of third party read/write access to the memory.

20. The system of claim 18, wherein the circuit further comprises means for receiving an identification of that certain person, the storage of the third party access parameters being governed by receipt of the identification.

21. The system of claim 20, wherein the means for receiving the identification comprises circuitry for receiving an identification code of the certain person, that identification code having been entered through the personal computing device and communicated over the communications link to the circuit.

* * * * *